United States Patent [19]

Schomberg

[11] Patent Number: 4,541,279

[45] Date of Patent: Sep. 17, 1985

[54] METHOD OF DETERMINING THE TIME-OF-FLIGHT OF AN ULTRASONIC PULSE

[75] Inventor: Hermann Schomberg, Hamburg, Fed. Rep. of Germany

[73] Assignee: U.S. Philips Corporation, New York, N.Y.

[21] Appl. No.: 551,613

[22] Filed: Nov. 14, 1983

[30] Foreign Application Priority Data

Nov. 16, 1982 [DE] Fed. Rep. of Germany ....... 3242284

[51] Int. Cl.[4] ............................................. G01N 29/00
[52] U.S. Cl. ...................................... 73/597; 73/602; 367/41
[58] Field of Search .......................... 73/597, 598, 602; 367/41

[56] References Cited

U.S. PATENT DOCUMENTS

| | | | |
|---|---|---|---|
| 2,989,726 | 6/1961 | Crawford et al. | 367/41 |
| 3,332,511 | 7/1967 | Silverman | 367/41 |
| 4,202,048 | 5/1980 | Edwards | 367/41 |
| 4,295,213 | 10/1981 | Mifsud | 367/41 |

*Primary Examiner*—Howard A. Birmiel
*Attorney, Agent, or Firm*—Jack E. Haken

[57] ABSTRACT

For the correction of the time-of-flight of an ultrasonic signal, the measurement signal (s) produced by an ultrasonic transducer (3) is digitized, stored and compared with a reference signal (s*). The comparison is performed by way of different relative shifts between the measurement signal and the reference signal. The value of the shift where both signals correspond best is used for the correction.

7 Claims, 6 Drawing Figures

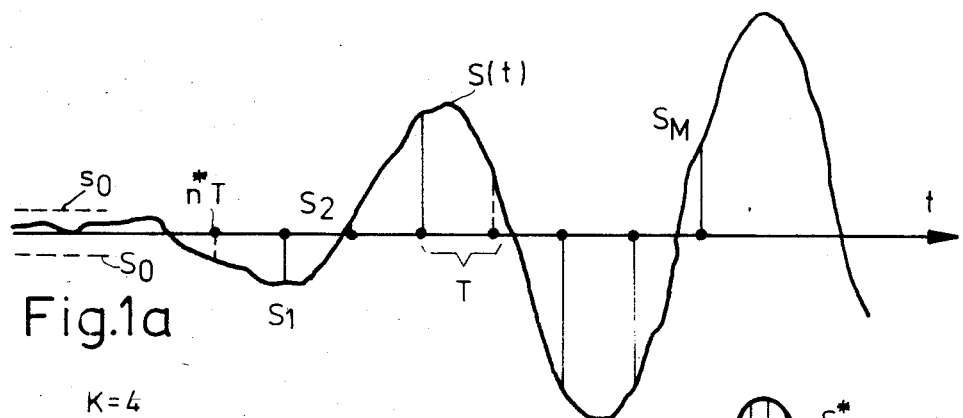
Fig.1a
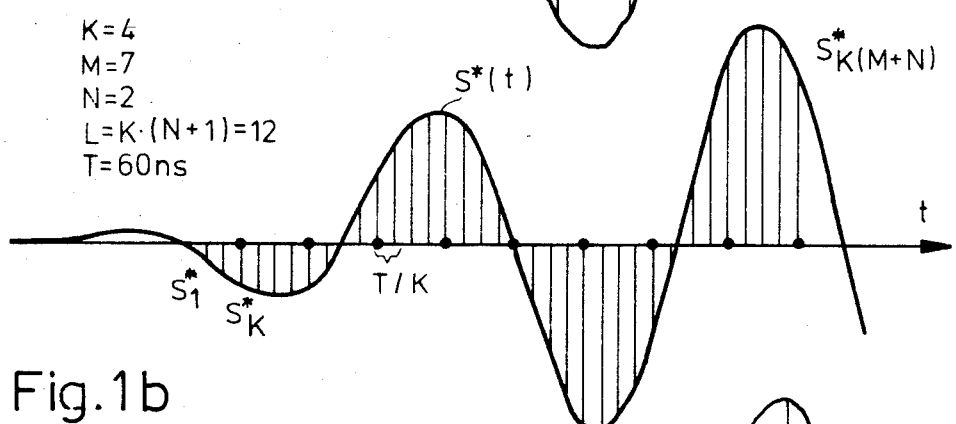
Fig.1b
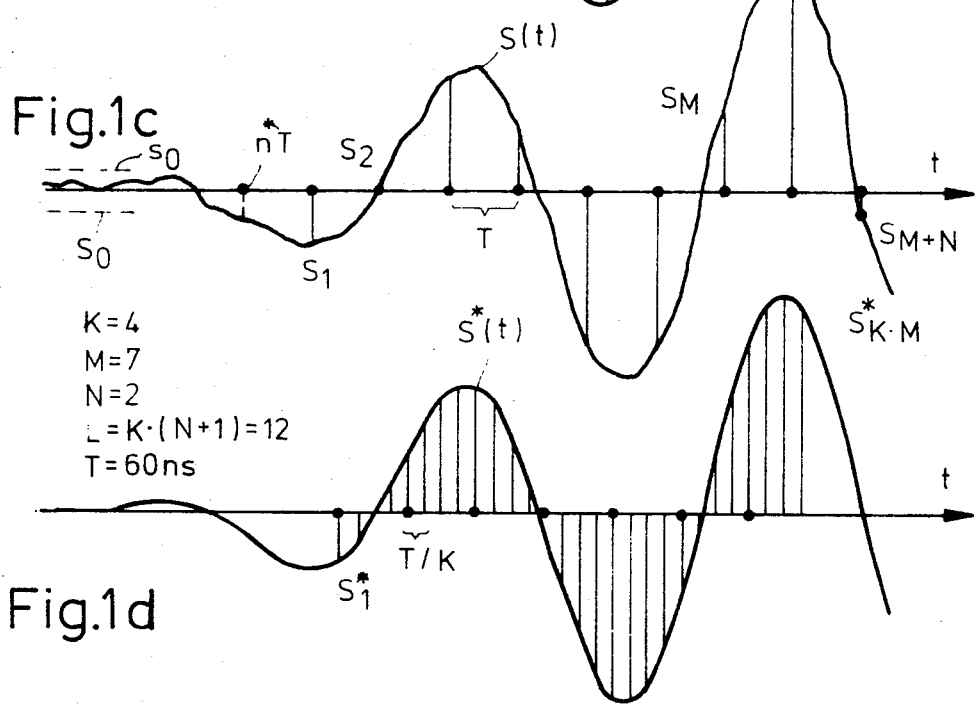
Fig.1c
Fig.1d

METHOD OF DETERMINING THE TIME-OF-FLIGHT OF AN ULTRASONIC PULSE

The invention relates to a method of determining the time-of-flight of an ultrasonic pulse which passes through an examination zone and which is converted into an electric measurement signal, the period of time being measured which expires between the instant of transmission of the ultrasonic pulse and the instant at which the measurement signal reaches a predetermined value.

A method of this kind is required, for example, in ultrasound computer tomography for the reconstruction of the acoustic refractive index distribution or the velocity distribution in the examination zone on the basis of the times-of-flight of successive ultrasonic pulses.

Methods and devices of this kind are known from U.S. Pat. Nos. 4,975,883 and 4,279,157. The known methods and devices produce an image of the refractive index distribution or the velocity distribution in a layer of an object present between an ultrasonic transmitter and an ultrasonic receiver. For a large number of points in this layer, a reconstruction unit determines these parameters on the basis of the measured times-of-flight of the ultrasonic pulses from the transmitter to the receiver. In order to make the reconstructed distribution correspond as well as possible to the actual distribution, inter alia the times-of-flight of the ultrasonic pulses must be very accurately determined, for example, with an accuracy of 20 ns.

In order to determine the time-of-flight, the known devices determine the period of time expiring between the instant of transmission of an ultrasonic pulse and the instant at which the signal received by the receiver exceeds a threshold value which is to be predetermined and which generally lies just above the interference level. The accuracy of such a time-of-flight measurement is adequate if the signals have at least approximately the same amplitude during the various measurements and if the interference, for example due to noise is comparatively low. However, these conditions are usually not satisfied in practice, so that inadmissibly large measurement errors are liable to occur.

It is the object of the invention to determine the time-of-flight with the necessary accuracy.

This object is achieved in accordance with the invention in that:

the measurement signal is sampled at a predetermined rate, the sampling values thus formed being stored, a section of the measurement signal formed by a series of sampling values is compared with an equally long section of a reference signal which is also stored in the form of a series of reference values, the section of the reference signal and possibly that of the measurement signal is repeatedly shifted over each time one sampling point, the shifted sections being compared again, the shift is determined where the correspondence of the sections is best, and the time-of-flight is determined by correction of the measured period of time in accordance with the shift of the sections thus obtained.

Like the known devices, the invention thus utilizes the comparatively inaccurate measurement of the time expiring between the instant of transmission of the ultrasonic pulse and the instant at which the measurement signal reaches a threshold value. This comparatively inaccurate value, however, is corrected.

The correction utilizes a reference signal which represents the characteristic variation in time of the measurement signal during non-disturbed operation and for a mean acoustic attenuation. The reference signal can be obtained, for example, in that an acoustically homogeneous medium is arranged between the transmitter and the receiver, so that the ultrasonic pulse is subject to a mean attenuation. The measurement signal thus obtained is sampled and stored in a memory. The measurement is repeated a number of times in the same circumstances, and a mean value is formed of the sampling values having occurred at the same instant (with respect to the transmission of the ultrasonic pulse) in order to eliminate the effect of interference (noise etc.). These mean values constitute the reference values and the series of reference values forms the reference signal. The reference signal thus obtained can be maintained for an indefinite period of time. In given circumstances, however, it may also be attractive to store several different reference signals for media which strongly deviate as regards velocity and attenuat on, each time the most suitable signal being used for the determination of the time-of-flight.

The correction is based on the idea that, with an appropriate shift in time the shape of the curve of the stored section of the measurement signal should correspond approximately to the shape of the curve of the reference signal. This shift in time is determined in that the sections are step-wise displaced with respect to one another over each time one sampling point, the shift being measured where the best correspondence is achieved between the sections of the measurement signal and the reference signal. Should the section of the measurement signal be shifted to later instants or should the section of the reference signal be shifted to earlier instants, the shift would be subtracted from the time measured at the beginning. In the other case it must be added thereto. It may also be necessary to add to the value thus corrected a value which is determined by the construction of the apparatus and the method chosen.

When the reference signal is stored with the same sampling point density as the measurement signal, the accuracy of the time-of-flight determination corresponds to the reciprocal value of the sampling rate. Therefore, in order to achieve the necessary accuracy it would be necessary to sample the measurement signal every 20 ns or even more often. This would necessitate the use of very fast digital-to-analog converters. Moreover, the number of sampling points to be stored in order to store a sufficiently long section would be comparatively large, thus prolonging the period of time required for determining the most suitable shift.

Therefore, in a preferred embodiment of the invention the reference signal is stored with a sampling point density which is a factor K larger than that of the measurement signal, each sub-series of the reference values constituting the section being formed from reference values wherebetween each time $K-1$ other reference values are situated in the series. The accuracy is thus enhanced, because the feasible shifts between the measurement signal and the reference signal may be smaller; the accuracy is now determined by the reciprocal value of the product of the sampling rate and the factor K. The number of sampling points used to store the measurement signal may then also be reduced by the factor K.

For the method in accordance with the invention it is merely necessary to store the sampling values which occur after the arrival of the ultrasonic pulse at the ultrasonic transducer generating the measurement signal. The preceding part of the output signal of the ultrasonic transducer, being formed exclusively by interference and noise, need neither be stored or sampled.

An embodiment in accordance with the invention will be described in detail hereinafter with reference to the accompanying drawing.

FIGS. 1a to 1d show the variation in time of a characteristic measurement signal and of the reference signal for both solutions described.

Figure 2:
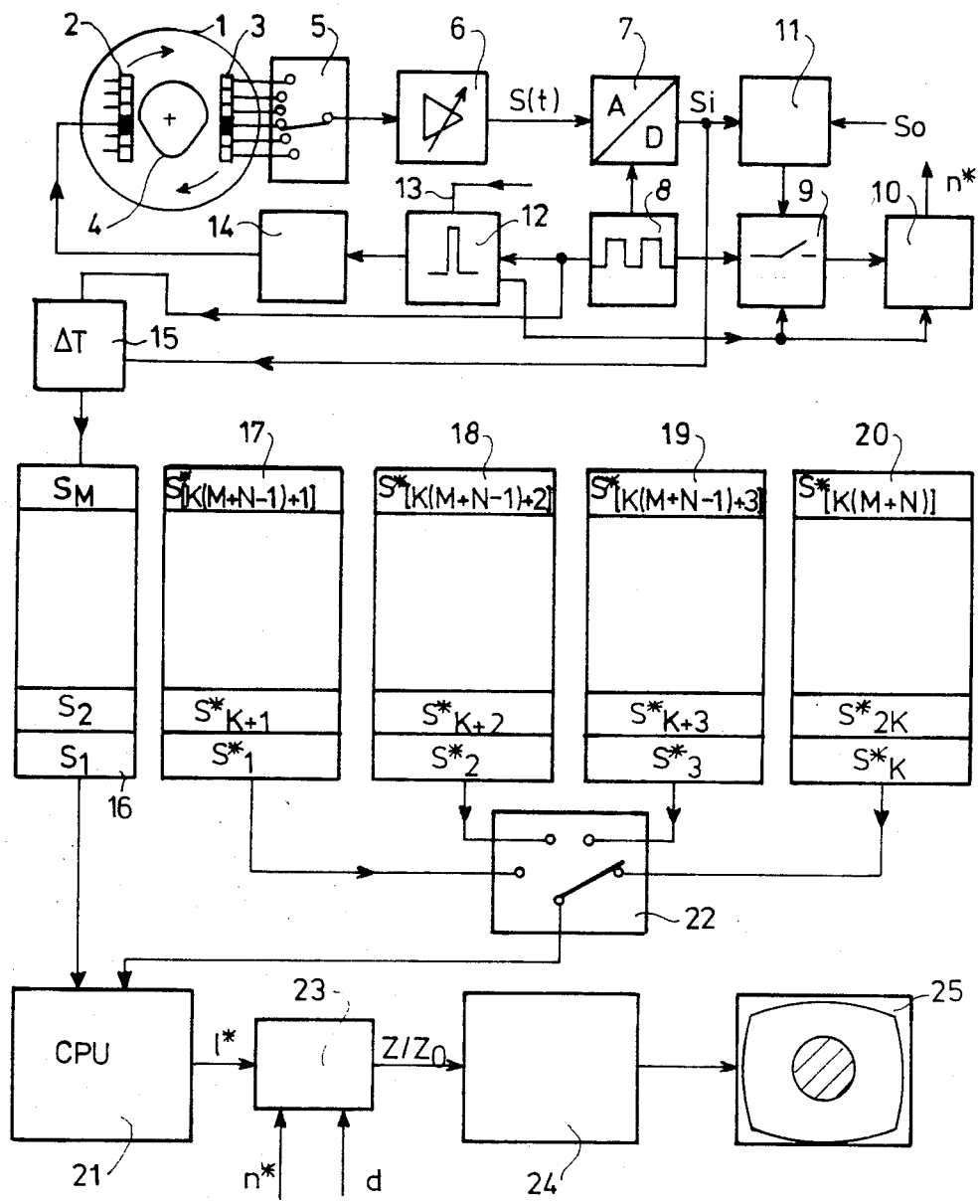
FIG. 2 shows a device in accordance with the invention for ultrasound examination.

FIG. 2 shows a cylindrical container (in a plan view) which is filled with a suitable liquid, for example, water. The container accommodates a large number (for example, 60) of ultrasonic transmitters 2 which are adjacently arranged in a straight row. The container 1 also accommodates a corresponding number of ultrasonic receivers 3 which are also adjacently arranged in a straight row, the rows 2 and 3 extending in parallel. The examination zone is situated between the two rows; the object 4 to be examined is arranged in this zone (this device is preferably used for examinations of the human breast).

For the determination of the time-of-flight, an ultrasonic transmitter is briefly activated. The ultrasonic pulse passes through the examination zone and hence through the object 4 and is subsequently converted into an electric signal by the oppositely situated ultrasonic receiver. This operation is repeated, be it that then neighbouring ultrasonic transducers transmit and receive, until all transducers have received and transmitted once. Subsequently, the ultrasonic transmitters 2 and the ultrasonic receivers 3, being mechanically interconnected in a manner not shown, are rotated through a small angle about an axis which extends perpendicularly to the plane of the drawing, after which the described operation is repeated, etc. After having been rotated through an angle of at least 180° in this manner, the ultrasonic transmitters 2 are displaced, together with the ultrasonic receivers 3, in a direction perpendicular to the plane of the drawing, so that layers which are situated deeper (or higher) can also be examined.

The outputs of the ultrasonic receivers 3 are connected, via a multiplexer 5, to the input of an amplifier 6 whose gain can be electronically adjusted and whose output signal is applied to an analog-to-digital converter 7. The gain of the amplifier 6 is chosen so that the output signal s thereof is at least approximately in the amplitude range which can be handled by the analog-to-digital converter. To this end, the gain may be corrected, for example in dependence of the peak value of the preceding measurement, because as a rule the attenuation is essentially the same during said preceding measurement.

The clock input of the analog-to-digital converter 7 is connected to the output of a clock generator 8 which generates a pulse-shaped clock signal having a period of, for example 60 ns. The output of the clock generator 8 is also connected, via a controllable switch 9, to the input of a counter 10. The controllable switch 9 is controlled by a comparator 11 which compares the binary numbers supplied by the analog-to-digital converter 7 with a binary number $s_0$ which is chosen so that it corresponds to a sampling value whose magnitude is slightly above the interference level. As soon as one of the sampling values $s_i$ becomes larger than the value $s_0$, the switch 9 is opened and remains open until the end of the time-of-flight measurement.

The clock generator 8 is also connected to the trigger input of a start pulse generator 12 which supplies a (single) start pulse when a suitable signal is present on its start input 13 and if at the same time the leading edge of a clock pulse appears on its trigger input. The start pulse activates an excitation circuit 14 which generates a pulse for the excitation of the ultrasonic transmitter which is at that instant assigned for flight-of-time measurement. Moreover, this start pulse closes the switch 9 and resets the counter 10. Consequently, the counter position is at any instant proportional to the period of time expired since the start pulse or the transmission of the ultrasonic pulse, and the counter position n* after the opening of the switch by the comparator 11 is proportional to the period of time expired between the transmission of the ultrasonic pulse and the instant at which one of the sampling values reaches or exceeds the value $s_0$.

The sampling values $s_i$ of the analog-to-digital converter are also applied to the input of a digital delay line 15 which is constructed as a shift register and whose output signal is delayed with respect to the input signal by as many clock pulses T as there are memory locations in the shaft register for the storage of sampling values. As will be described in detail hereinafter, the digital delay line 15 may be omitted in given circumstances. The output of the digital delay line is connected to the data input of a shift register 16 which comprises M memory locations (for example, M=7) and whose clock input (not shown) is also controlled by the clock pulses of the clock generator 8. After activation of the comparator 11 (after the opening of the switch 9), M further sampling values are applied to the digital delay line 15 and M sampling values are stored in the shift register 16. If the digital delay line 15 were absent, therefore, the sampling values $s_1 \ldots s_M$ would be the first M sampling values after the reaching or exceeding of the threshold value $s_0$. However, if the shift register forming the digital delay line 15 comprises memory locations for p sampling values $s_i$ (p<M), the sampling values $s_1 \ldots s_{p-1}$ are the last p−1 sampling values before the reaching of the threshold value, whilst $s_p$ is the first sampling value which is larger than $s_0$, the other values being the directly subsequent sampling values. After the storage of said M sampling values in the shift register 16, this operation is terminated. To this end there may be provided, for example a counter (not shown) which is reset by the output signal of the comparator 11 and which interrupts, for example the clock line between the clock generator 8 and the digital delay circuit 15.

Subsequently, the shift register 16 is coupled end-around so that when a clock pulse is applied, each sampling value is moved to the memory location which was previously occupied by the directly preceding sampling value during sampling, i.e. the sampling value $s_M$ now occupies the memory location previously occupied by the sampling values $s_{M-1}$, $s_2$ occupies the memory location of $s_1$, and $s_1$ occupies the memory location of $s_M$. The shift register 16 may also be formed by a random access memory whose address counter is controlled in known manner so that the memory acts as a shift register for the environment. The sampling values, however, do not change their memory location therein.

For the description of the further signal processing reference is first made to FIG. 1a and FIG. 1b. FIG. 1a shows the variation in time of a signal s on the output of the amplifier 6. The broken lines s₀ represent the interference level superposed on the signal. This signal is sampled at the sampling rate 1/T (T=60 ns), which means that a sampling value is obtained every 60 ns, even before the first negative part of the signal s exceeds the negative threshold value s₀; "exceed" is to be understood to mean herein that the absolute value of s is larger than the absolute value of s₀. Between this instant and the instant of transmission of the ultrasonic pulse, a period of time n*T has expired, n* thus indicating the position of the counter 10. Subsequently, M further sampling values s₁ ... s_M are measured and stored in the shift register 16 in the described manner. In that case the delay 15 line may be omitted.

The sampling rate T must be adapted to the ultrasonic oscillation s(t) so that the signal s can be sampled several times between the zero crossings. For the indicated value of T (60 ns), the frequency of the ultrasonic oscillation may amount to, for example 3.5 MHz. M, i.e. the number of sampling values, is chosen so that a representative part of the signal s can be measured. As has already been stated, M=7 is a suitable value.

FIG. 1b shows the variation in time of the reference signal s*. Again a representative part of this signal is sampled and the sampling values, now being referred to as reference values, are stored in a memory device. However, the sampling point density, i.e. the number of reference values per unit of time, is now a factor K larger, K being an integer number, for example 4. This corresponds to a sampling rate K/T, i.e. the reference signal is sampled every 15 ns.

A further difference with respect to the measurement signal consists in that the section of the reference signal for which reference values are stored is larger than the corresponding time interval of the measurement signal s. The number of reference values amounts to K (M+N), N being an integer number which determines the maximum feasible value of the correction and which amounts to, for example 2.

The value n*T which represents the period of time expiring between the instant of transmission of the ultrasonic pulse and the instant at which the threshold value S₀ is exceeded only approximates the actual time-of-flight of the ultrasonic pulse; this is on the one hand because of the reasons already described and on the other hand because of the comparatively long duration of the sampling period (T=60 ns). In order to correct this comparatively inaccurate value, the reference signal is "shifted" with respect to the measurement signal (or vice versa) until the corresponding signal sections coincide; the value n*T is then corrected in accordance with this "shift".

The determination of the value of this correction is actually the finding of a series of reference values which corresponds as well as possible to the sampling values s₁ ... s_M. The accuracy of this correction is determined by the value T/K, i.e. the time-of-flight can be accurately determined up to the value T/K=15 ns, though the measurement signal is sampled only every 60 ns.

For determining the value of the correction, first a function F(a,l) is formed in accordance with the relation:

$$F(a,l) \sum_{m=1}^{M} (as_m - s^*K(m + N) + 1 - l)^2 \quad (1)$$

The value of F(a,l) is a measure of the deviation between the section of the measurement signal defined by the sampling values s₁ ... s_m and brought to scale by the factor a, and a section of corresponding length in the reference signal which is determined by the parameter l. The factor a serves to take into account the fact that for a fixed l the "accuracy of fit" is also dependent on the amplitude of the measurement signal. However, a restriction to positive values should be made.

The value to be found is the value l*, for which the function F(a,l) has a minimum value. This is obtained via the following consideration:

$$F(a,l) = a^2 \cdot A - 2a \cdot B(l) + C(l) \quad (2)$$

$$A = \sum_{m=1}^{M} s_m^2 \quad (3)$$

$$B(l) = \sum_{m=1}^{M} s_m \cdot s^*K(m+N)+1-l \quad (4)$$

$$C(l) = \sum_{m=1}^{M} (s^*K(m+N)+1-l)^2 \quad (5)$$

For a fixed l, F(a,l) becomes minimum as a function of a at the most where $$\frac{\partial F(a \cdot l)}{\partial a} = 0.$$

This is the case for $$a(l) = B(l)/A \quad (6)$$

When the value a(l) is substituted for a in the formula (2) and the value thus obtained is referred to as G(l), the following formule is obtained:

$$G(l) = -B^2(l)/A + C(l) \quad (7)$$

Therefore, it suffices to find the value of l for which G(l) has an absolute minimum. However, it is to be noted that G(l) may exhibit subsidiary minimum values. The range in which the shift takes place, however, is chosen so that in addition to the desired principal minimum it includes no more than one subsidiary minimum. The principal minimum is then characterized by the additional condition a>0 or, in accordance with (6), B(l)>0. In accordance with formule (3), for the calculation of G(l) it is necessary to calculate the variable A from the sampling values and the variable B(l) from formule (4) for each l of the sampling values and the corresponding reference values. The variable C(l) (formule (5)) is independent of the measurement signal and, therefore, it may already have been stored in a suitable memory. From the values of A, B(l) and C(l) thus formed, G(l) can be calculated in accordance with the formule (7). The value l* for which G(l) has a minimum is used for the correction in that the value l*T/K is added to the expression n*T. The value G(l*), i.e. the minimum of the function G(l), is a measure of the quality of the adaptation between the sampling values and the series of reference values defined by 1*: the smaller the continuously non-negative value G(1*), the better the correspondence between the measurement signal and the reference signal and the more accurate the value 1* found will be.

However, the described calculation can be simplified further by taking into account the fact that the value A is independent of 1 and that C(1) is modified only slightly when 1 is incremented or decremented by 1. This is because, subject to the additional condition B(1)>0, the function G(1) then has a minimum when B(1) has a maximum; it is then merely necessary to determine the maximum of B(1), which is possible by way of small arithmetical operation. The variable B(1), moreover, offers a digital version of the so-called short-time cross-correlation function (see Woschni "Informationstechnik", second edition, 1976, VEB-Verlag Technik Berlin, page 161) between the measurement signal and the reference signal which is a measure of the correlation of the two signals s and s*. However, the magnitude of the maximum value B(1*) does not provide an unambiguous indication of the quality of the adaptation between the sampling values and the reference values, because B(1*) is not only dependent on this adaptation but also on the fluctuations of the amplitude of the analog signal on the input of the analog-to-digital converter 7. After having found the value 1* for which B(1) becomes maximum, G(1*) can be calculated in order to be used as a quality measure for the accuracy of fit. This requires slightly less arithmetical work than the calculation in advance of all values G(1).

Figure 3:
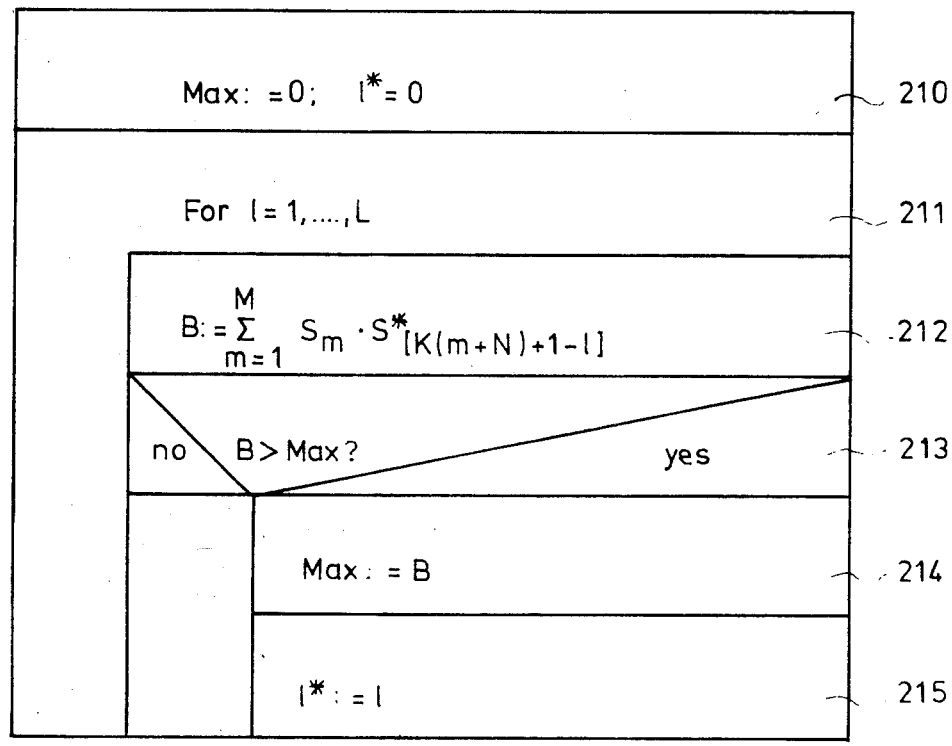
FIG. 3 shows a flowchart for the determination of 1*.

The determination of the maximum value of B(1) will be described in detail hereinafter with reference to FIG. 2 and the flowchart of FIG. 3.

The reference values are stored in four memory devices 17, 18, 19 and 20 which may be constructed as shift registers; however they are preferably formed by a programmable read-only memory (PROM) whose address counter is controlled so that the values can be successively fetched. Each of the memories 17 ... 20 comprises at least M+N memory locations, so at least nine memory locations in the present example. In the memory 17 there are stored the first reference value and every $K^{th}$ (fourth) subsequent reference value, i.e. the reference values $s^*_1, s^*_{K+1} \ldots, s^*_{K(m+N-1)+1}$. In the second memory 18 there are stored the values $s^*_2 \ldots s^*_{K(m+N-1)+2}$, and in the $K^{th}$ memory, i.e. in the fourth memory 20, there are stored the values $s^*_K \ldots s^*_{K(m+N)}$. It is alternatively possible to store all reference values in a single memory. Instead of successive reference values, only each $K^{th}$ reference value should then be stored, so for example $s^*_K, s^*_{2K} \ldots$ etc., at the memory locations bearing successive addresses, thus simplifying the addressing during later processing. The outputs of the four memories are connected to an arithmetic unit 21 via a multiplexer 22. The arithmetic unit 21 also receives the values $s_1 \ldots s_m$ stored in the shift register 16.

The arithmetic unit 21 determines the value 1* for which B(1) has a maximum. This can be achieved by means of a suitably programmed microcomputer. The structure diagram (nassi-Schneiderman diagram) used by the microcomputer to determine the value 1* is shown in FIG. 3. After the storage of the values $s_1 \ldots s_M$ in the shift register 16, the comparison value Max and also the value 1* are set to 0 in the first step 210. The second step 211 represents a loop which is completed L times $(L=K(N+1)=12)$. The first step 212 of the loop is the calculation of the value B, first of all for the value 1=1. This step represents a sub-routine during which first the value $s_1$ is fetched from the memory 16 and the value $s^*_{K(m+N)}=s^*_{3K}$ is fetched from the memory 20. These values are multiplied by one another. To this product there is added the product of the values $s_2$ and $s^*_{4K}$ etc. until during the seventh step the sampling value $s_M$ and the reference value $s^*_{K(M+N)}$ are fetched, multiplied by one another and added to said sum. All reference values are then fetched from the memory 20.

After calculation of the value B in the described manner, it is compared with the comparison value Max during the step 213. If the calculated value B(1) is larger than the comparison value Max, the calculated value B is assigned to the comparison value Max (step 214) and each time the value of 1, so in this case 1, is assigned to the value 1* (step 215). Subsequently, or if the test 213 reveals that the calculated value B is not larger than the comparison value, the calculation returns to the first step 212 of the program loop 211, however, 1 then being set to 2. For the calculation of B the reference values $s^*_{2K+3} \ldots s^*_{K(M+N-1)+3}$ from the memory 19 are multiplied by the associated values $s_1 \ldots s_M$ from the memory 16; it is then necessary for the multiplexer to connect the output of this memory 19 to the data input of the arithmetic unit 21. The interrogation operation 213 is then completed again, the values Max and 1* being modified again or not, depending on whether the newly calculated value is larger than the (in given circumstances) already modified comparison values Max, after which the next step (with 1=3) is repeated. The steps 212, 213 and possibly 214, 215 are completed a total number of twelve times. As a rule, the maximum of the values B(1) to B(12) and the associated value 1* have been determined. Only in the case 1*=0 (step 210) all B values would have been negative. This case is indicative of some kind of error and, therefore, it can be used to eliminate the effect of this obviously incorrect value on the reconstruction.

Thus far it has been assumed that the variables B(1) and G(1) have to be formed for all values of 1, i.e. for $1=1 \ldots L$ $(L=K(N+1))$. However. this range of values could be limited for each measurement if the position of a characteristic part of the measurement signal s, for example of the first positive maximum were known (in FIG. 1 this would be $s_3$). To this end, it is merely necessary to determine the first positive maximum of the series and the range in which 1 is varied is limited depending on near which of the values $s_1$ to $s_M$ this maximum is situated. The calculation time can thus be reduced.

The arithmetic unit 21 can be constructed by means of a suitably programmed microprocessor. This microprocessor is also capable of performing further control functions, for example, the addressing of the memories 17 to 20 and the control of the shift register 16 and the multiplexer 22. The generating of the start pulse on the line 13, the comparison of the sampling values $s_i$ with the threshold value $s_0$ and the counting of the pulses of the clock generator could also be performed by means of this microprocessor; the microprocessor could even supply the clock pulses itself. The arithmetical operations to be performed by the arithmetic unit are comparatively simple (multiplication, summing and comparison). The arithmetic unit can alternatively be formed by suitable contemporary bitslice processors which are faster than a single microprocessor.

When calculations with a fixed decimal point are used for the calculation of B(1) or G(1), being attractive in view of the calculation speed, overflow is liable to occur for intermediate results. This can be prevented by means of suitable so-called scaling steps.

In a summing stage 23 the time-of-flight Z is formed in accordance with the relation $$Z = n^* T + 1^* T/K - d \qquad (8)$$

Therein, n* is the content of the counter 10 and d is an apparatus constant. The value of this constant has to be determined only once in a comparatively simple manner by determining, the circumstances otherwise being the same, the time-of-flight for two different distances between the transmitters and receivers in accordance with the formule (8), the value d being varied so that the times-of-flight determined by way of the formule (8) are proportional to the distances between the ultrasonic transmitters and receivers. Depending on the type of amplifier 6 used, moreover, d may also be dependent on the gain factor chosen. This dependency, however, is known in advance so that it can be readily taken into account.

The velocity of sound in a medium depends on the temperature thereof. For a liquid medium such as water the dependency is such that the time-of-flight over a path of a few centimetres can already vary by more than the value T/K in reaction to a temperature variation of a few tenths of a degree, so that the measurement would become excessively inaccurate already on the basis of such temperature dependencies. One possibility of avoiding such incorrect measurements is to keep the temperature of the liquid in the reservoir 1 constant. However, the effect of temperature on the time-of-flight can alternatively be substantially eliminated. To this end, in each angular position of the ultrasonic transmitter 2 and the receiver 3 the time-of flight $Z_0$ of an ultrasonic pulse can be determined which has not been influenced by the object 4 to be examined, the geometrical distance between the transmitter and the receiver being the same. This is usually the case for the extreme ultrasonic transmission and receiving elements of the ultrasonic transducer rows 2 and 3. The time-of-flight $Z_0$ determined on the basis of the values n* and 1* thus measured in accordance with the formula (8) is dependent on the temperature in substantially the same way as the time-of-flight Z of an ultrasonic pulse which is influenced by the object 4 and which is determined shortly thereafter. Therefore, the quotient $Z/Z_0$ is a value which is substantially independent of the temperature and which is proportional to the time-of-flight. This quotient is applied to a computer 24 which calculates the refractive index distribution at the various points of a layer of the object 4 being examined. The calculated distribution is displayed on a suitable display apparatus 25, for example a television monitor.

Some alternative versions of the methods described thus far are feasible. For example, in the expression (1) for F(a,1) the factor a can also be applied to the reference signal. The same considerations as used above then lead to the determination of the minimum of $$G'(1) = A - B(1)^2 / C(1) \qquad (9)$$

with the sub-condition B(1) > 0. Essentially this is equivalent to the determination of the maximum of B(1). The expressions A, B(1), C(1) in (9) are as defined in (3), (4), (5). Contrary to the value G(1) in accordance with (7), the value of the minimum G(1*) does not provide an indication of the reliability of the result.

In the method described thus far a search is made for the first negative sampling value whose absolute value exceeds a predetermined threshold value $s_0$. However, it may be more advantageous instead to search for the first position sampling value which exceeds a positive threshold value $s_0'$; $s_0'$ may then also be larger than $s_0$. In the example shown in FIG. 1a this is the case, for example for $s_3$. However, in order to store the sampling values $s_1$ to $s_M$ also for this version, use can be made of the delay line 15 for which p = 3 in this case.

Alternatively, a positive and a negative threshold could be combined; the continuous storage could then be started, for example only when the negative threshold is exceeded in the more negative direction and the positive threshold is exceeded in the more positive direction in rapid succession.

Thus far it has been assumed that the section of the reference signal determined by reference values is larger than the section of the measurement signal determined by sampling values. However, the method in accordance with the invention can also be performed when the section of the measurement signal defined by the sampling values is made larger so that, for example M + N sampling values are available (see FIG. 1c) and the corresponding section of the reference signal is reduced so that only K·M reference values are present (FIG. 1d).

The correspondence of the relevant sections of the reference signal and the measurement signals can then be numerically described again by a function F(a,1) which satisfies the following relation:

$$F(a,l) = \sum_{m=1}^{M} (a \cdot s_{x(m,l)} - s^*_{y(m,l)})^2 \qquad (10)$$

Therein, it is assumed that:

$$x(m,l) = m + \text{int}((l-1)/K) \qquad (11)$$

and $$y(m,l) = K \cdot m - (l-1) + K \cdot \text{int}((l-1)/K) \qquad (12)$$

Therein, int ( ) is function which corresponds to the largest integer number which is not larger than the argument ( ) of this function.

In this case the function F(a,1) reaches the minimum value for the 1 for which the expression $$G(1) = -B^2(1)/A(1) + C(1)$$

becomes minimum, where now $$A(l) = \sum_{m=1}^{M} (s_{x(m,l)})^2 \qquad (13)$$

$$B(l) = \sum_{m=1}^{M} s_{x(m,l)} \cdot s^*_{y(m,l)} \qquad (14)$$

$$C(l) = \sum_{m=1}^{M} s^*_{y(m,l)}{}^2 \qquad (15)$$

The minimizing of G(1) is essentially equivalent again to the maximizing of B(1); alternatives analogous to the first solution are again feasible. The calculation of 1*, therefore, corresponds to the described method, so that this description need not be repeated.

What is claimed is:

1. In a method for determining the time-of-flight of an ultrasound pulse through an examination zone which is disposed between an ultrasound transmitter and an ultrasound receiver which comprises the steps of:

transmitting an ultrasound pulse through the examination zone;

receiving the pulse after it has traveled through the examination zone and producing an electrical received signal (s) therefrom;

periodically sampling the received signal (s) at a predetermined rate 1/T and storing the sequences of samples thus produced;

measuring the discrete period of time (N*T) between the time of transmission and the time that the sampled received signal reaches a predetermined threshold value;

calculating a correction factor by: comparing the stored sequence of samples of the received signal with sequences of periodic samples of a discrete reference signal (s*), repeatedly shifting the samples of the reference signal by one sample position and again comparing the received signal sequence to the shifted reference signal until a shifted position of the reference signal which produces a best correspondence between the samples of the received signal and the samples of the shifted reference signal is determined, and then choosing the associated shift of the reference signal as the correction factor;

and adding the correction factor to the interval (n*T) to determine the time-of-flight;

wherein, as an improvement:

the reference signal (s*) has a sampling density which is a factor K larger than sampling of the stored signal (s), and wherein the stored signal is compared with sequences which consist of every $K^{th}$ sample of the reference signal.

2. In a method for determining the time-of-flight of an ultrasound pulse through an examination zone which is disposed between an ultrasound transmitter and an ultrasound receiver which comprises the steps of:

transmitting an ultrasound pulse through the examination zone;

receiving the pulse after it has traveled through the examination zone and producing an electrical received signal (s) therefrom;

periodically sampling the received signal (s) at a predetermined rate 1/T and storing the sequence of samples thus produced;

measuring the discrete period of time (N*T) between the time of transmission and the time that the sampled received signal reaches a predetermined threshold value;

calculating a correction factor by: comparing the stored sequence of samples of the received signal with sequences of periodic samples of a discrete reference signal (s*), repeatedly shifting the samples of the reference signal by one sample position and again comparing the received signal sequence to the shifted reference signal until a shifted position of the reference signal which produces a best correspondence between the samples of the received signal and the samples of the shifted reference signal is determined, and then choosing the associated shift of the reference signal as the correction factor;

and adding the correction factor to the interval (n*T) to determine the time-of-flight;

wherein, as an improvement:

the reference signal is produced by measuring the mean received value of an ultrasound pulse which is propagated through a homogeneous medium using the same transmitting and receiving apparatus and geometry as are used to measure the examination zone.

3. In a method for determining the time-of-flight of an ultrasound pulse through an examination zone which is disposed between an ultrasound transmitter and an ultrasound receiver which comprises the steps of:

transmitting an ultrasound pulse through the examination zone;

receiving the pulse after it has traveled through the examination zone and producing an electrical received signal (s) therefrom;

periodically sampling the received signal (s) at a predetermined rate 1/T and storing the sequency of samples thus produced;

measuring the discrete period of time (N*T) between the time of transmission and the time that the sampled received signal reaches a predetermined threshold value;

calculating a correction factor by: comparing the stored sequence of samples of the received signal with sequences of periodic samples of a discrete reference signal (s*), repeatedly shifting the samples of the reference signal by one sample position and again comparing the received signal sequence to the shifted reference signal until a shifted position of the reference signal which produces a best correspondence between the samples of the received signal and the samples of the shifted reference signal is determined, and then choosing the associated shift of the reference signal as the correction factor;

and adding the correction factor to the interval (n*T) to determine the time-of-flight;

wherein, as an improvement:

the reference signal (s*) has a sampling density which is a factor K larger than sampling of the stored signal (s), and wherein the stored signal is compared with sequences which consist of every $K^{th}$ sample of the reference signal, and the reference signal is produced by measuring the mean received value of an ultrasound pulse which is propagated through a homogeneous medium using the same transmitting and receiving apparatus and geometry as are used to measure the examination zone.

4. A method as claimed in claim 1, 2 or 3 wherein the step of choosing the correction factor comprises:

forming a plurality of values G(l) in accordance with the relation $$G(l) = -B(l)^2/A(l) + C(l)$$

in which l is a variable integer number and in which $$A(l) = \sum_{m=1}^{M} s_m^2$$

-continued $$B(l) = \sum_{m=1}^{M} s_m s^*_{y(m,l)}$$

$$C(l) = \sum_{m=1}^{} (s^*_{y(m,l)})^2$$

in which $s_m$ is the $m^{th}$ measured signal sample value and $s^*y(m,l)$ is the yth reference signal sample value, and $y(m,1)=K(m+N)+1-1$, in which N and K are integer numbers and the number K is equal to the quotient of the sample point density of the reference signal divided by that of the measurement signal, determining the value 1* for which G(1) is minimum, subject to the subsidiary condition B(1)>0, and in which the time-of-flight Z is corrected in accordance with the relation $$Z = n^*T + 1^*T/K - d,$$

in which T is the reciprocal value of the sampling rate and d is a predetermined apparatus parameter.

5. A method as claimed in claim 4, characterized in that the short-time cross-correlation function B(1) of the measurement signal (s) and of the reference signal (s*) is formed by means of the sampling values ($s_x$) and the reference values ($s^*_y$), that value of 1 being determined for which the short-time cross-correlation function B(1) has an absolute maximum.

6. A method as claimed in claim 1, 2 or 3 in which the step of choosing the correction factor comprises forming a plurality of values G(1) in accordance with the relation $$G(1) = B(1)^2/A(1) + C(1)$$

in which 1 is a variable integer number and in which $$A(l) = \sum_{m=1}^{M} (s_{x(m,l)})^2$$

$$B(l) = \sum_{m=1}^{M} s_{x(m,l)} \cdot s^*_{y(m,l)}$$

$$C(l) = \sum_{m=1}^{M} (s^*_{y(m,l)})^2$$

in which $s_x$ is the $x^{th}$ measured signal sample value and $s^*y$ is the yth reference signal sample value, and for which $x(m,1) = m + \text{int} ((1-1)/K)$ $y(m,1) - Km + 1 - 1 + K \text{ int} ((1-1)/K)$ K being an integer number equal to the quotient of the sample point density of the reference signal divided by that of the measurement signal;

determining the value 1* for which G(1) is a minimum, subject to the subsidiary condition B(1)>0, and in which the time-of-flight Z is corrected in accordance with the relation $$Z = n^*T + 1^*T/K - d$$

in which T is the reciprocal value of the sampling rate and d is a predetermined apparatus parameter.

7. A method as claimed in claim 6 wherein the short-time cross-correlation function B(1) of the measurement signal (s) and of the reference signal (s*) is formed by means of sampling values ($s_x$) and the reference values ($s^*y$), that value of 1 being determined for which the short-time cross-correlation function B(1) has an absolute maximum.

* * * * *